(12) United States Patent
Lorenz et al.

(10) Patent No.: US 11,324,565 B2
(45) Date of Patent: May 10, 2022

(54) STAND FOR A SURGICAL MICROSCOPE, SURGICAL MICROSCOPY SYSTEM, AND METHOD FOR OPTIMIZING AN ASSEMBLY SPACE OF A SURGICAL MICROSCOPY SYSTEM

(71) Applicant: Carl Zeiss Meditec AG, Jena (DE)

(72) Inventors: Axel Lorenz, Meißen (DE); Patrick Berghoff, Aalen (DE); Michael Mühlbeyer, Elchingen (DE); Jürgen Groß, Aalen (DE); Christian Wolf, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 253 days.

(21) Appl. No.: 16/575,118

(22) Filed: Sep. 18, 2019

(65) Prior Publication Data

US 2021/0077218 A1    Mar. 18, 2021

(51) Int. Cl.
*A61B 90/25* (2016.01)
*G02B 21/00* (2006.01)
*G02B 21/24* (2006.01)

(52) U.S. Cl.
CPC .......... *A61B 90/25* (2016.02); *G02B 21/0012* (2013.01); *G02B 21/24* (2013.01)

(58) Field of Classification Search
CPC .... G02B 21/0012; G02B 21/24; G02B 7/001; A61B 90/20; A61B 90/25
See application file for complete search history.

(56) References Cited

U.S. PATENT DOCUMENTS

| 9,622,830 | B2 | 4/2017 | Christ et al. | |
|---|---|---|---|---|
| 9,885,858 | B2 | 2/2018 | Ernsperger et al. | |
| 2013/0099072 | A1* | 4/2013 | Butler | A61B 90/50 248/124.1 |
| 2015/0267860 | A1* | 9/2015 | Schutz | B60B 33/0078 248/424 |
| 2018/0014893 | A1* | 1/2018 | Cleary | A61B 34/30 |

* cited by examiner

*Primary Examiner* — Stephone B Allen
*Assistant Examiner* — Adam W Booher
(74) *Attorney, Agent, or Firm* — Falk Ewers; Ewers IP Law PLLC

(57) ABSTRACT

A stand for a surgical microscope and a method for optimizing an assembly space of a surgical microscopy system are provided. The stand includes a base part, a stand part forming a c-shape structure, having a first end and a second end, and being mounted on the base part at the first end. The stand part has a hollow structure with reinforcements arranged within the hollow structure and the reinforcements extend vertically through the entire hollow structure. The stand part may include a first stand part element and a second stand part element, and the first and second stand part elements are arranged at a horizontal distance relative to one another and form together the c-shape structure. The method includes relocating electronic components from the arms to an area of the stand part thereby shifting a center of gravity of the stand.

17 Claims, 8 Drawing Sheets

900

```
┌─────────────────────────────────────────────┐
│    RELOCATING A PLURALITY OF ELECTRONIC     │
│ COMPONENTS FROM A PLURALITY OF ARMS TO AN AREA │──905
│    BETWEEN A BEARING AND A BASE PART OF A STAND │
│  PART THEREBY SHIFTING A CENTER OF GRAVITY OF A │
│   STAND FROM A FIRST CENTER POSITION TO A SECOND │
│                CENTER POSITION              │
└─────────────────────────────────────────────┘
                       │
                       ▼
┌─────────────────────────────────────────────┐
│      CONNECTING THE PLURALITY OF ELECTRONIC     │──910
│ COMPONENTS TO AT LEAST ONE MOUNTING ELEMENT ON │
│                 THE STAND PART              │
└─────────────────────────────────────────────┘
```

*FIG. 9*

STAND FOR A SURGICAL MICROSCOPE, SURGICAL MICROSCOPY SYSTEM, AND METHOD FOR OPTIMIZING AN ASSEMBLY SPACE OF A SURGICAL MICROSCOPY SYSTEM

TECHNICAL FIELD

The invention relates to a stand for a surgical microscope, a surgical microscopy system, and a method for optimizing an assembly space of a surgical microscopy system.

BACKGROUND

A surgical microscope for installation on the floor in the middle price segment (midrange) typically includes a stand, a microscope head, and a suspension mechanism for mounting the microscope head on the stand. The suspension mechanism can be, e.g., a yoke.

These surgical microscopes are typically used in the field of neurosurgery or otolaryngology. Some stands for surgical microscopes have a Selective Compliance Assembly Robot Arm (SCARA) design, i.e., the stands have two parallel vertical axes and associated support arms which allow positioning of the microscope head in a horizontal plane.

If one of the support arms has a parallel kinematics (also referred to as carrier arm or boom arm) in the vertical plane, the degree of freedom is extended by the stroke range so that a spatial positioning of the microscope head is possible while maintaining the orientation of the microscopy head.

The setting of desired working positions (according to the situation in the operating theatre) is typically carried out via handles on the microscope head which causes the support arms to pivot around the axes.

Even during the surgical procedure, fine positioning is carried out via the handles on the microscope head to change the viewing angle or in the event of a collision with other devices. In both cases, low movement forces are required, and automatic unintentional movements (drift) of the microscope head must be avoided.

Many electronic components including cables are utilized in modern surgical microscopes to realize optical functionalities, video imaging, illumination, digital control and communication. These are not only masses on the support arms that need to be moved during the positioning of the microscope head, but also, because the cables have to be guided along the rotational axes, resistance forces are generated during rotational movements about the axes by the cables. Therefore, there has been a need to lower the bearing frictions to lower the resistance forces.

In addition to the effects on the movement forces, the SCARA support arms always form disturbing contours in the field of view of the surgical personal. In other words, direct eye contact in the operating theatre is disturbed, as is the field of view of all participants on assistance devices or screens.

As a result, there has been a continuing need to make the stand parts including the support arms unobtrusive and compact with the necessary strength and sufficient stiffness in appearance. Furthermore, attachments to the support arms interfere with the operating environment, especially during pivoting, and also lead to collisions with other system components. Therefore, there has been a continued need to reduce these attachments on the support arms. The same applies to the fixed stand areas (such as consoles or base parts), which must be as compact as possible to avoid interfering contours.

SUMMARY

It is therefore an object of the present invention to improve the assembly space of a surgical microscopy system and to reduce disturbing contours in the surgical microscopy system.

The object is achieved by a stand for a surgical microscope including a base part, a stand part forming a c-shape structure, having a first end and a second end, and being mounted on the base part at the first end, and the stand part having a hollow structure with reinforcements arranged within the hollow structure and the reinforcements vertically extending through the entire hollow structure.

According to an aspect of the disclosure, the stand part includes a first stand part element and a second stand part element. The first and second stand part elements are arranged at a horizontal distance relative to one another and form together the c-shape structure.

The stand part includes a connecting part arranged at the second end of the stand part, a plurality of mounting elements arranged on inner surfaces of the first and second stand part elements to mount at least one electronic component on the stand part between the connecting part and the base part, and a cover which encloses the at least one electronic component.

According to another aspect of the disclosure, the at least one electronic component includes a personal computer, a video device, a power supply device, a light source, a network interface component, and a radio-frequency identification (RFID) reader.

According to yet another aspect of the disclosure, the stand further includes a plurality of arms arranged on the stand part, the plurality of arms being connected to one another by rotary joints defining at least three rotation axes and being configured to displace a surgical microscope head, mounted on one of the plurality of arms via a suspension mechanism, in three directions of a coordinate system.

The plurality of arms includes a carrier arm. The carrier arm includes at least one first bearing and at least one second bearing, a first shaft arranged in the at least one first bearing, and a second shaft arranged in the at least one second bearing, and the at least one first bearing and the at least one second bearing are directly mounted on the carrier arm.

According to an aspect of the disclosure, the carrier arm is a first carrier arm, the plurality of arms includes a second carrier arm having a third bearing, the first shaft is arranged in a recess on the connecting part and defines a first rotation axis of the at least three rotation axes, and the second shaft is arranged in the third bearing and defines a second rotation axis of the at least three rotation axes.

The object is also achieved by surgical microscopy system comprising including a stand including a base part and a stand part, the stand part including a first stand part element and a second stand part element and having a first end and a second end, the stand part being mounted on the base part at the first end, the stand part including a plurality of mounting elements arranged on inner surfaces of the first and second stand part elements, the first and second stand part elements being arranged at a horizontal distance relative to one another and forming together a c-shape structure, each of the first and second stand part elements having a hollow structure with reinforcements arranged within the hollow structure and the reinforcements vertically extending through the entire hollow structure, a connecting part arranged at the second end of the stand part, at least one electronic component arranged between the connecting part and the base part and being connected to the at least one mounting element on the stand part, a plurality of arms arranged on the stand part, a surgical microscope head mounted on one of the plurality of arms, and the plurality of arms being connected to one another by rotary joints defining at least three rotation axes and being configured to displace the surgical microscope head in three directions of a coordinate system.

According to an aspect of the disclosure, the at least one electronic component includes a personal computer, a video device, a power supply device, a light source, a network interface component, and a radio-frequency identification (RFID) reader.

According to another aspect of the disclosure, surgical microscopy system further includes a plurality of arms arranged on the stand part, the plurality of arms being connected to one another by rotary joints defining at least three rotation axes and being configured to displace a surgical microscope head mounted on one of the plurality of arms in three directions of a coordinate system.

The plurality of arms includes a carrier arm, the carrier arm includes at least one first bearing and at least one second bearing, a first shaft arranged in the at least one first bearing, and a second shaft arranged in the at least one second bearing, and the at least one first bearing and the at least one second bearing are directly mounted on the carrier arm.

According to a further aspect of the disclosure, the carrier arm is a first carrier arm, the plurality of arms includes a second carrier arm having a third bearing, the first shaft is arranged in a recess on the connecting part and defines a first rotation axis of the at least three rotation axes, and the second shaft is arranged in the third bearing and defines a second rotation axis of the at least three rotation axes.

The object is further achieved by a method for optimizing an assembly space of a surgical microscopy system, the surgical microscopy system including a stand including a base part and a stand part, the stand part including a first stand part element and a second stand part element and having a first end and a second end, the stand part being mounted on the base part at the first end, the stand part including a plurality of mounting elements arranged on inner surfaces of the first and second stand part elements, the first and second stand part elements being arranged at a horizontal distance relative to one another and forming together a c-shape structure, each of the first and second stand part elements having a hollow structure with reinforcements arranged within the hollow structure and the reinforcements vertically extending through the entire hollow structure, a connecting part arranged at the second end of the stand part, a plurality of arms arranged on the stand part, the surgical microscope head mounted on one of the plurality of arms, the plurality of arms being connected to one another by rotary joints defining at least three rotation axes and being configured to displace the surgical microscope head in three directions of a coordinate system, and a plurality of electronic components arranged on the plurality of arms, the method including relocating the plurality electronic components from the plurality of arms to an area between the connecting part and the base part of the stand part thereby shifting a center of gravity of the stand from a first center position to a second center position, and connecting the plurality of electronic components to the at least one mounting element on the stand part.

The first center position is defined at a first horizontal distance and a first vertical distance from a center of the base part based on first locations of the plurality of electronic components on the plurality of arms, the second center position is defined at a second horizontal distance and a second vertical distance from the center of the base part based on second locations of the plurality of electronic components in the area between the connecting part and the base part of the stand part, the first horizontal distance is larger than the second horizontal distance, and the first vertical distance is larger than the second horizontal distance.

According to an aspect of the disclosure, the method further includes reducing motion forces required for positioning the surgical microscopy head in the surgical microscopy system by the shifting of the center of gravity of the stand from the first center position to the second center position and by the connecting of the plurality of electronic components to the at least one mounting element on the stand part.

According to yet another aspect of the disclosure, the method further includes reducing a drift of the surgical microscopy head by the shifting of the center of gravity of the stand from the first center position to the second center position and by the connecting of the plurality of electronic components to the at least one mounting element on the stand part.

According to a further aspect of the disclosure, the plurality of electronic components includes a personal computer, a video device, a power supply device, a light source, a network interface component, and a radio-frequency identification (RFID) reader.

According to an aspect of the disclosure, the plurality of arms includes a carrier arm, the carrier arm includes at least one first bearing and at least one second bearing, a first shaft arranged in the at least one first bearing, and a second shaft arranged in the at least one second bearing, and the method further includes directly mounting the at least one first bearing and the at least one second bearing on the carrier arm, and reducing an interfering contour of the carrier arm by reducing a cross section of the carrier arm, the interfering contour being a contour which interferes with a field of view of a person operating the surgical microscopy system.

According to another aspect of the disclosure, the method further includes reducing the interfering contour of the surgical microscopy system by the relocating of the plurality electronic components from the plurality of arms to the area between the connecting part and the base part of the stand part, and the reducing of the cross section of the carrier arm.

BRIEF DESCRIPTION OF THE DRAWINGS

The invention will now be described with reference to the drawings wherein:

FIG. 9 shows a flow chart of a method for optimizing an assembly space of a surgical microscopy system according to an exemplary embodiment of the disclosure.

DESCRIPTION OF EXEMPLARY EMBODIMENTS

Exemplary embodiments of the disclosure will be explained below with reference to the accompanying schematic figures. Features that coincide in their nature and/or function may in this case be provided with the same designations throughout the figures.

The terms "exhibit", "have", "comprise" or "include" or any grammatical deviations therefrom are used in a non-exclusive way. Accordingly, these terms can refer either to situations in which, besides the feature introduced by these terms, no further features are present, or to situations in which one or more further features are present. For example, the expression "A exhibits B", "A has B", "A comprises B" or "A includes B" may refer both to the situation in which no further element aside from B is provided in A (that is to say to a situation in which A is composed exclusively of B) and to the situation in which, in addition to B, one or more further elements are provided in A, for example element C, elements C and D, or even further elements.

Furthermore, the terms "at least one" and "one or more" and grammatical modifications of these terms or similar terms, if they are used in association with one or more elements or features and are intended to express the fact that the element or feature can be provided singly or multiply, in general are used only once, for example when the feature or element is introduced for the first time. When the feature or element is subsequently mentioned again, the corresponding term "at least one" or "one or more" is generally no longer used, without restriction of the possibility that the feature or element can be provided singly or multiply.

Also, the terms "preferably", "in particular", "by way of example" or similar terms are used in conjunction with optional features, without alternative embodiments thereby being restricted. In this regard, features introduced by these terms are optional features, and there is no intention to restrict the scope of protection of the claims, and in particular of the independent claims, by these features. In this regard, the invention, as will be recognized by a person of ordinary skill in the art, can also be carried out using other configurations. Similarly, features introduced by "in one embodiment of the invention" or "in one exemplary embodiment of the invention" are to be understood to be optional features, without this being intended to restrict alternative refinements or the scope of protection of the independent claims. Furthermore, all possibilities of combining the features introduced by these introductory expressions with other features, whether optional or non-optional features, are intended to remain unaffected by said introductory expressions.

Figure 1:
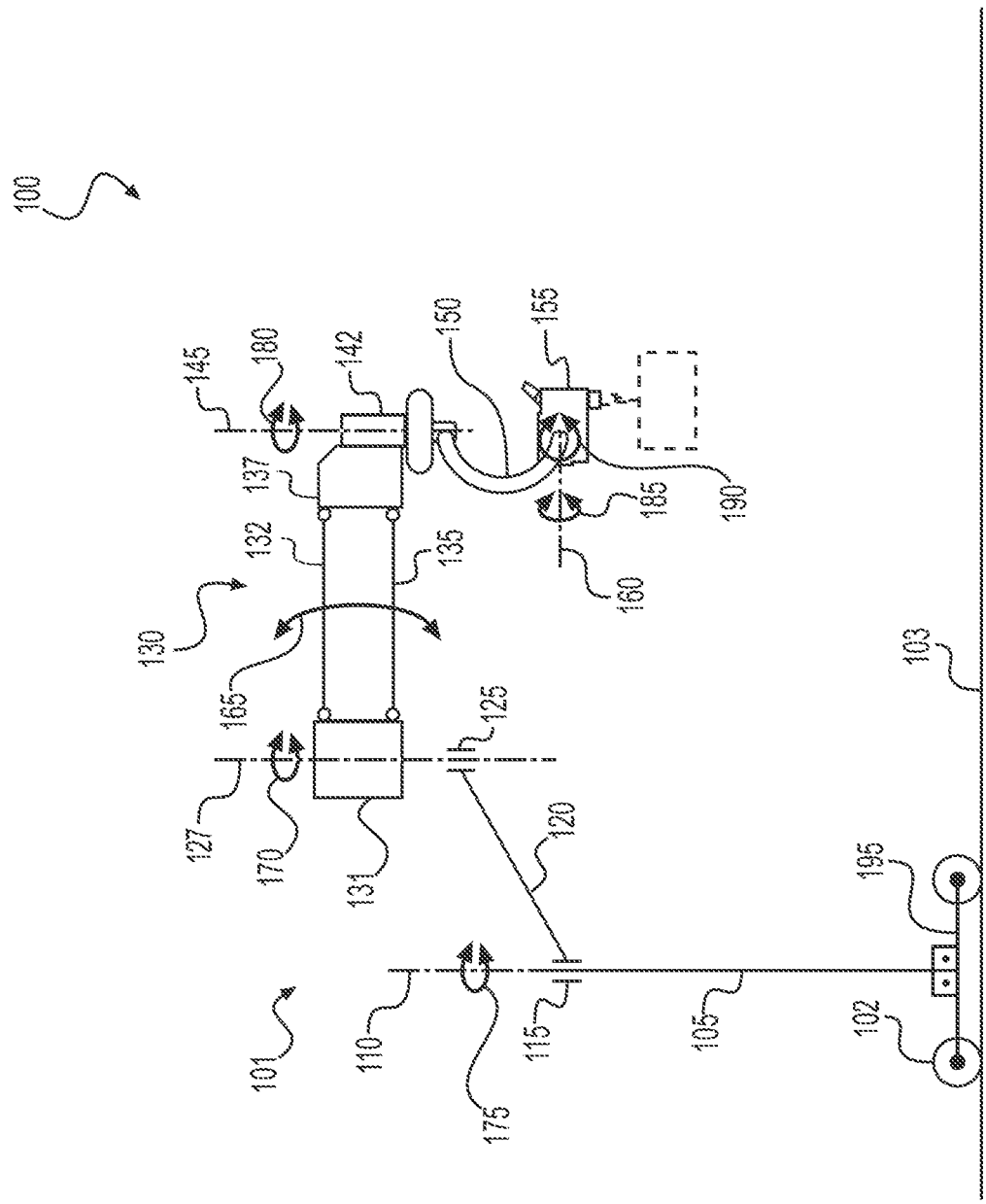
FIG. 1 shows a schematic illustration of surgical microscopy system according to an exemplary embodiment of the invention.

FIG. 1 shows a schematic illustration of surgical microscopy system 100. The surgical microscopy system 100 includes stand 101 and a microscope head 155. Stand 101 has a base part 195, a stand part 105, a first carrier arm 120, and a second carrier arm 130. The second carrier arm 130 has a first carrier arm part 132 and a second carrier arm part 135 forming a parallel kinematics.

The stand 101 further includes a connection element 137 on which the first carrier arm part 132 and the second carrier arm part 135 are pivotably mounted. The microscope head 155 is also mounted on the connection element 137 via a suspension mechanism which includes connection element 142 and yoke 150.

As shown in FIG. 1, the base part 195 has rollers 102 to move the surgical microscopy system 100 to a designated position in the operating theatre. At the designated position, the rollers are locked such that during normal operation, i.e., during a surgery, the stand 101 (and thereby the entire surgical microscopy system 100) is immovably fixed on the floor 103.

As shown in FIG. 1, the stand part 105 is fixedly mounted on the base part 195 and defines a first vertical axis 110. The first carrier arm 120 has bearings 115 and 125 and is mounted in bearing 115 pivotably about the first axis 110 on the stand part 105, as indicated by arrows 175. The bearing 125 defines a second vertical axis 127 which is parallel to the first vertical axis 110. The second carrier arm 130 includes a part 131 which is mounted pivotably about the second vertical axis 110 on the first carrier arm 120, as indicated by arrows 170.

By pivoting the first carrier arm 120 and the second carrier arm 130 about the first vertical axis 110 and the second vertical axis 127, respectively, the microscope head 155 can be moved in a horizontal plane. In addition, the first carrier arm part 132 and the second carrier arm part 135 of the second carrier arm 130 which form the parallel kinematics are pivotable in the vertical plane about a third axis, as indicated by arrows 165, thereby providing a degree of freedom which allows a spatial positioning of the microscope head 155 in all three directions of a coordinate system while maintaining the orientation of the microscopy head 155.

In addition, connection element 142 and yoke 150 of the suspension mechanism may include further bearings which allow the microscopy head 155 to be pivoted about a fourth axis 145 as indicated by arrows 180, about a fifth axis 160, as indicated by arrows 185, and about a sixth axis as indicated by arrows 190.

Figure 2:
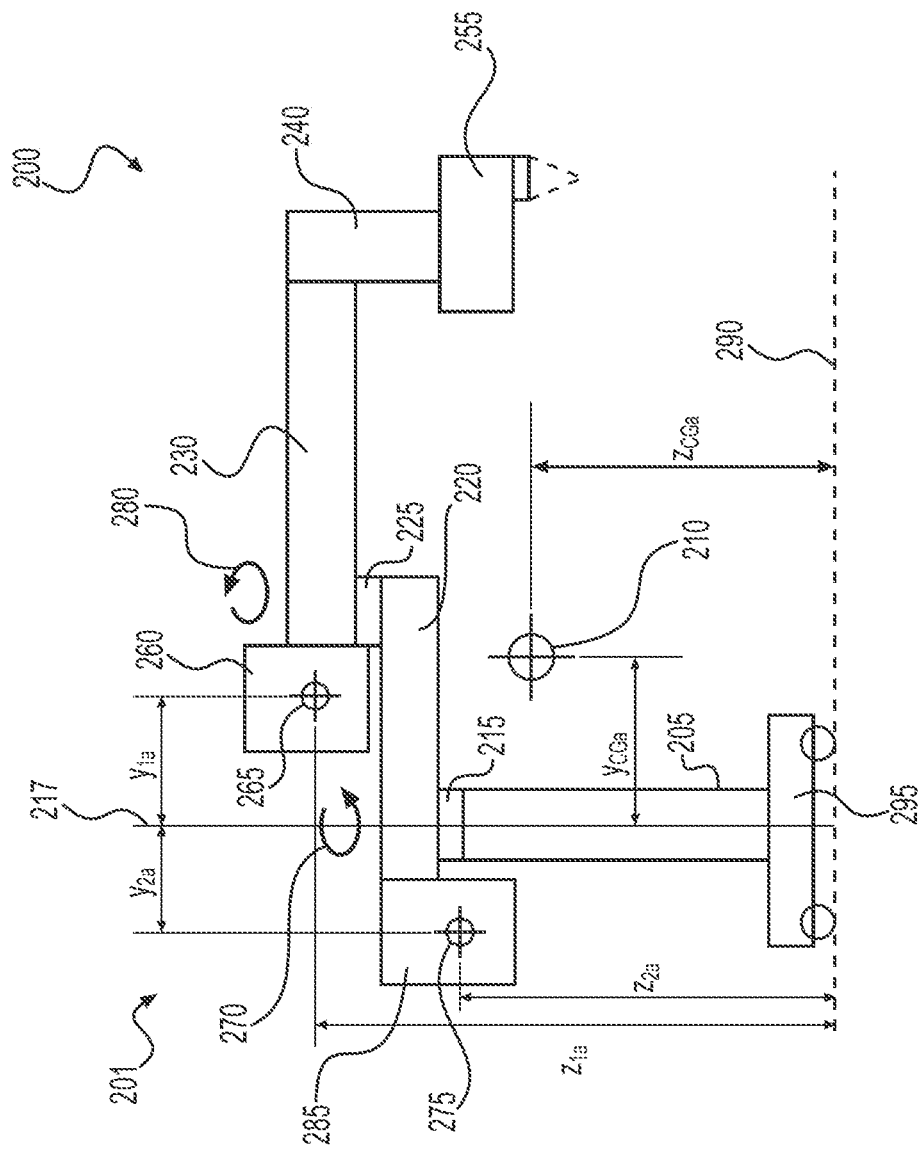
FIG. 2 shows a schematic illustration of a surgical microscopy system known from the related art.

Referring now to FIG. 2 which shows a schematic illustration of surgical microscopy system 200 including a stand 201 known from the related art. Stand 201 includes a stand part 205 mounted on a base part 295. Stand 201 further includes a first carrier arm 220 mounted in a bearing 215 pivotably about a first axis indicated by arrows 270. A second carrier arm 230 is mounted on the first carrier arm 220 in bearing 225 pivotably about a second axis as indicated by arrows 280. Surgical microscopy system 200 further includes a microscope head 255 mounted on the second carrier arm 230 via suspension mechanism 240.

FIG. 2 shows electronic components 260 and 285, having centers of gravity (CG) 265 and 275, respectively. Electronic component 260 is mounted on the second carrier arm 230 and electronic component 285 is mounted on the first carrier arm 220. The center of gravity 265 of the electronic component 260 is defined by a horizontal distance $Z_{1a}$ from the floor 290 and a vertical distance $Y_{1a}$ from the axis 217. The center of gravity 275 of the electronic component 285 is defined by a horizontal distance $Z_{2a}$ from the floor 290 and a vertical distance $Y_{2a}$ from the axis 217.

The centers of gravity 265 and 275 together with the centers of gravity of all other elements of the stand 201 result in an overall center of gravity 210 of the stand 201 of the surgical microscopy system 200. The position of the center of gravity 210 of the stand 201 is defined at a first horizontal distance $Z_{CGa}$ from the floor 290 and a first vertical distance $Y_{CGa}$ from the axis 217.

Figure 3:
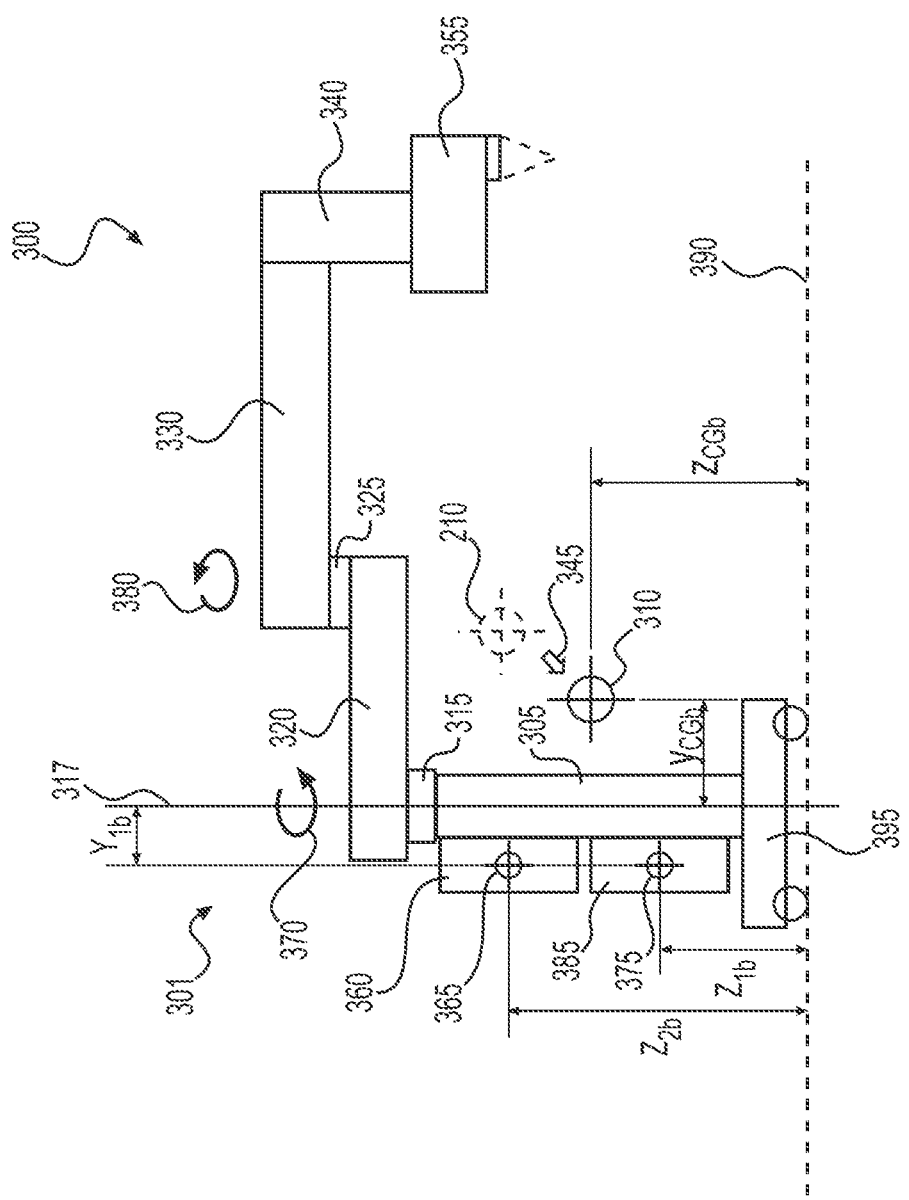
FIG. 3 shows a schematic illustration of a surgical microscopy system according to an exemplary embodiment of the disclosure.

FIG. 3 shows a schematic illustration of surgical microscopy system 300 including a stand 301 according to an exemplary embodiment of the disclosure. Stand 301 includes a stand part 305 in the form of a post or pillar mounted on a base part 395. Stand 301 further includes a first carrier arm 320 mounted in a bearing 315 pivotably about a first axis indicated by arrows 370. A second carrier arm 330 is mounted on the first carrier arm 320 in bearing 325 pivotably about a second axis as indicated by arrows 380. Surgical microscopy system 300 further includes a microscope head 355 mounted on the second carrier arm 330 via suspension mechanism 340.

The base part 395 has rollers to move the surgical microscopy system 300 to a designated position in the operating theatre. At the designated position, the rollers are locked such that during normal operation, i.e., during a surgery, the stand 301 (and thereby the entire surgical microscopy system 300) is immovably fixed on the floor 390.

As shown in FIG. 3, to reduce dynamic forces, the electronic components 360 and 385 are mounted on the stand part 305 below the bearing 315 instead of being mounted on the carrier arms 320 and 330. As a result, the position of the center of gravity 365 of the electronic component 360 is defined at a horizontal distance $Z_{2b}$ from the floor 290 and a vertical distance $y_{1b}$ from the axis 317. The position of the center of gravity 375 of the electronic component 385 is defined at a horizontal distance $z_{1b}$ from the floor 290 and also at the vertical distance $Y_{1b}$ from the axis 317. However, other arrangements are possible as long as the electronic components are all mounted on the stand part 305 at positions below bearing 315.

This does not only reduce the masses moved in the surgical microscopy system 300, but also positively shifts, as indicated by arrow 345, the center of gravity of the stand 301 from the first position 210 at which the center of gravity of the stand 201 in FIG. 2 is defined to a second position 310 at which the center of gravity of the stand 301 is defined which is significantly closer to the base part 395 and which results in a mass centralization. The second position 310 is defined at a horizontal distance $Z_{CGb}$ from the floor 390 and at a vertical distance $Y_{CGb}$ from the axis 317. In addition, since the stand 301 is immovably fixed on the floor 390 during normal operation, a sliding position of the stand 301 is clearly defined and due to moving the electronic components below bearing 315, the need for an elaborately rotatable push handle can be eliminated.

In addition, shifting the center of gravity of the stand 301 to the position 310 reduces a drift of the surgical microscopy head.

Electronic components include a personal computer, a video device, a power supply device, a light source, a network interface component, and a radio-frequency identification (RFID) reader, but are not limited thereto. Any other electronic component that can be mounted on the carrier arms 320 and 330 can also be moved to positions on the stand 301 below bearing 315.

Figure 4:
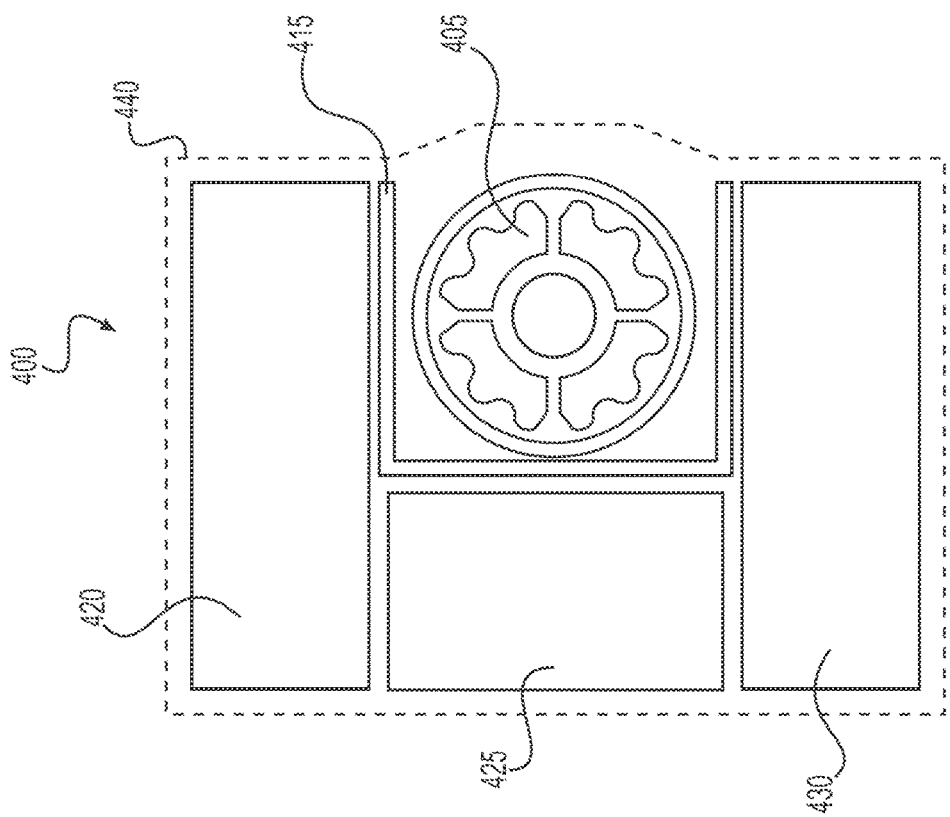
FIG. 4 shows a top plan view of a stand part known from the related art.

FIG. 4 shows a top plan view of a stand part 400 known from the related art. Stand part 400 includes a circular post or pillar 405 which is mounted on a base part (not shown). A holding plate 415 is mounted on the post 405 and electronic components 420, 425, and 430 are mounted on holding plate 415 around the post 405 and covered by cover 440.

Figure 5:
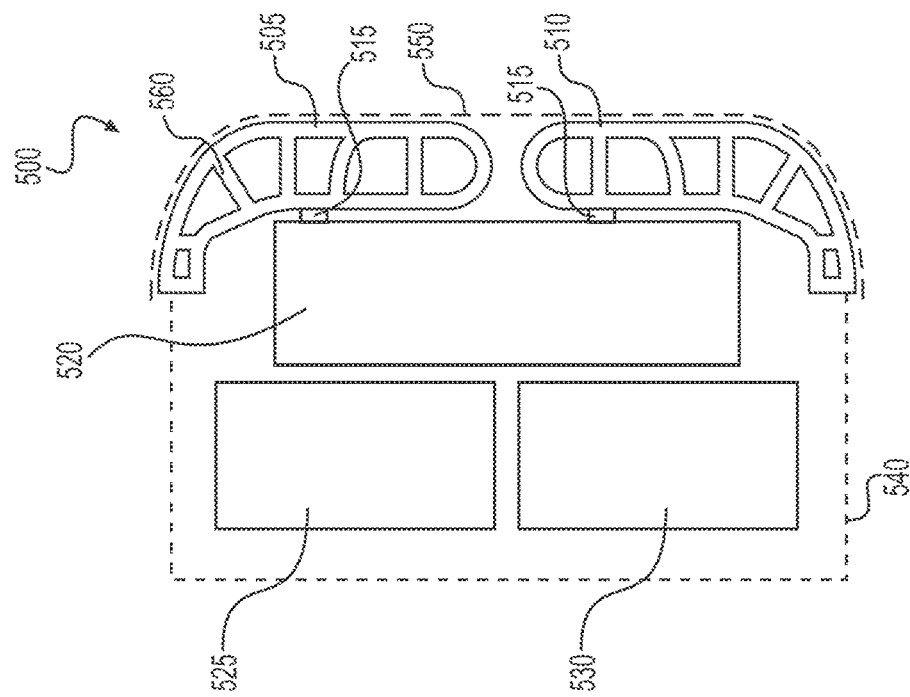
FIG. 5 shows a top plan view of a stand part according to an exemplary embodiment of the disclosure.

FIG. 5 shows a top plan view of a stand part 500 according to an exemplary embodiment of the disclosure. Stand part 500 includes a first stand part element 505 and a second stand part element 510. The first and second stand part elements are arranged at a horizontal distance relative to one another and form together the c-shape structure. Although not shown in FIG. 5, instead of providing two separate stand part elements, stand part 500 can also be formed by a single stand part element forming the c-shape structure.

Each of the first stand part element 505 and the second stand part element 510 has a hollow structure with reinforcements 560 arranged within the hollow structure. The reinforcements 560 extend vertically through the entire hollow structures of the first and second stand part elements. This structure is also called self-supporting exoskeleton.

As shown in FIG. 5, the first stand part element 505 and the second stand part element 510 include a plurality of mounting elements 515 arranged on inner surfaces of the first and second stand part elements to directly or indirectly mount the electronic components 520, 525, and 530 on the stand part 500. The dash line 550 indicates an uncovered area. In addition, stand part 500 includes cover 540 which encloses the electronic components 520, 525, and 530.

Figure 6:
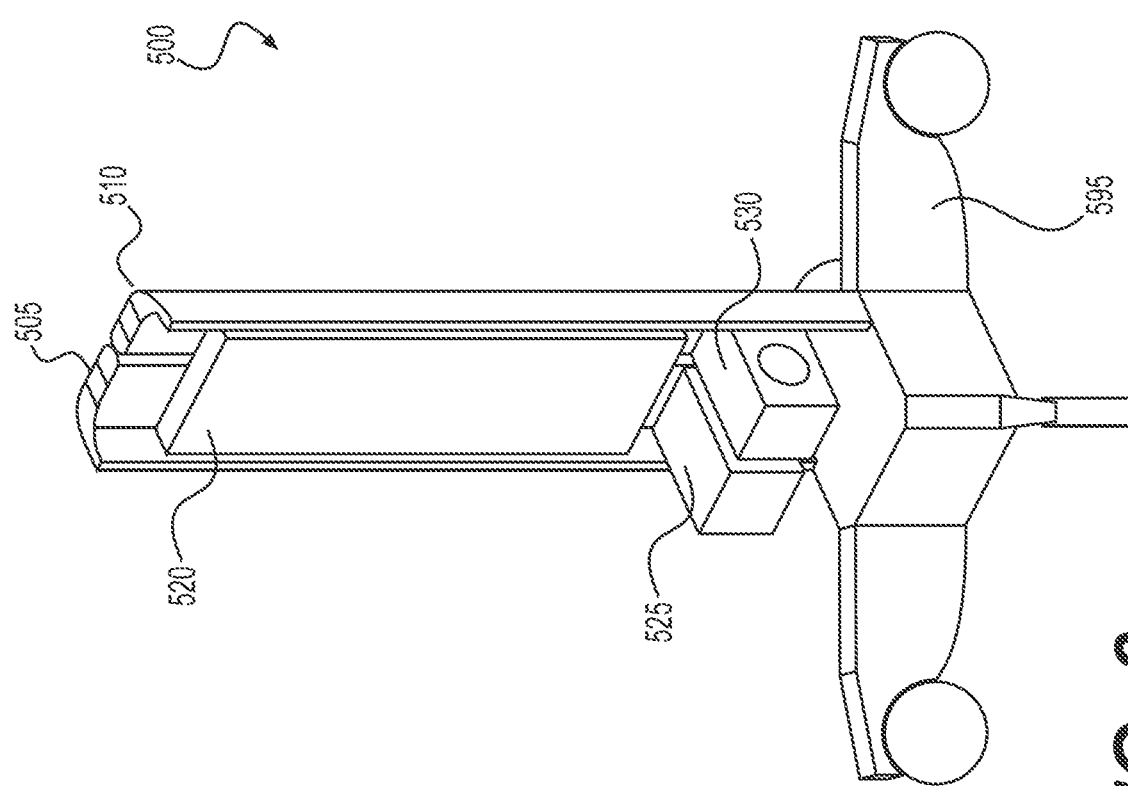
FIG. 6 shows a perspective plan view of the stand part shown in FIG. 5.

FIG. 6 shows a perspective view of stand part 500 shown in FIG. 5 without cover 540. As shown in FIG. 6, the first stand part element 505 and the second stand part element 510 are fixedly mounted on the base part 595. Stand part 500 also includes a connecting part (not shown) which has a recess in which a shaft can be mounted and which is arranged at an end of the of the stand part elements 505 and 510 opposite to the base part 595.

Thus, in order to minimize the disturbance contour of the stand, the functional separation in the area of the post 405 between load-bearing function and component holding function is resolved by the stand part 500. Instead of providing a post 405 and a holding plate 415, a quasi-self-supporting exoskeleton 505 and 510 is provided which allows the available installation space to be optimally utilized. The design of the self-supporting exoskeleton 505 and 510 as a visible surface also eliminates the need for additional covers in this area.

The C-shaped supporting structure consisting of double columns, which was selected on the basis of existing electronic components, is to be regarded as an example.

Figure 7:
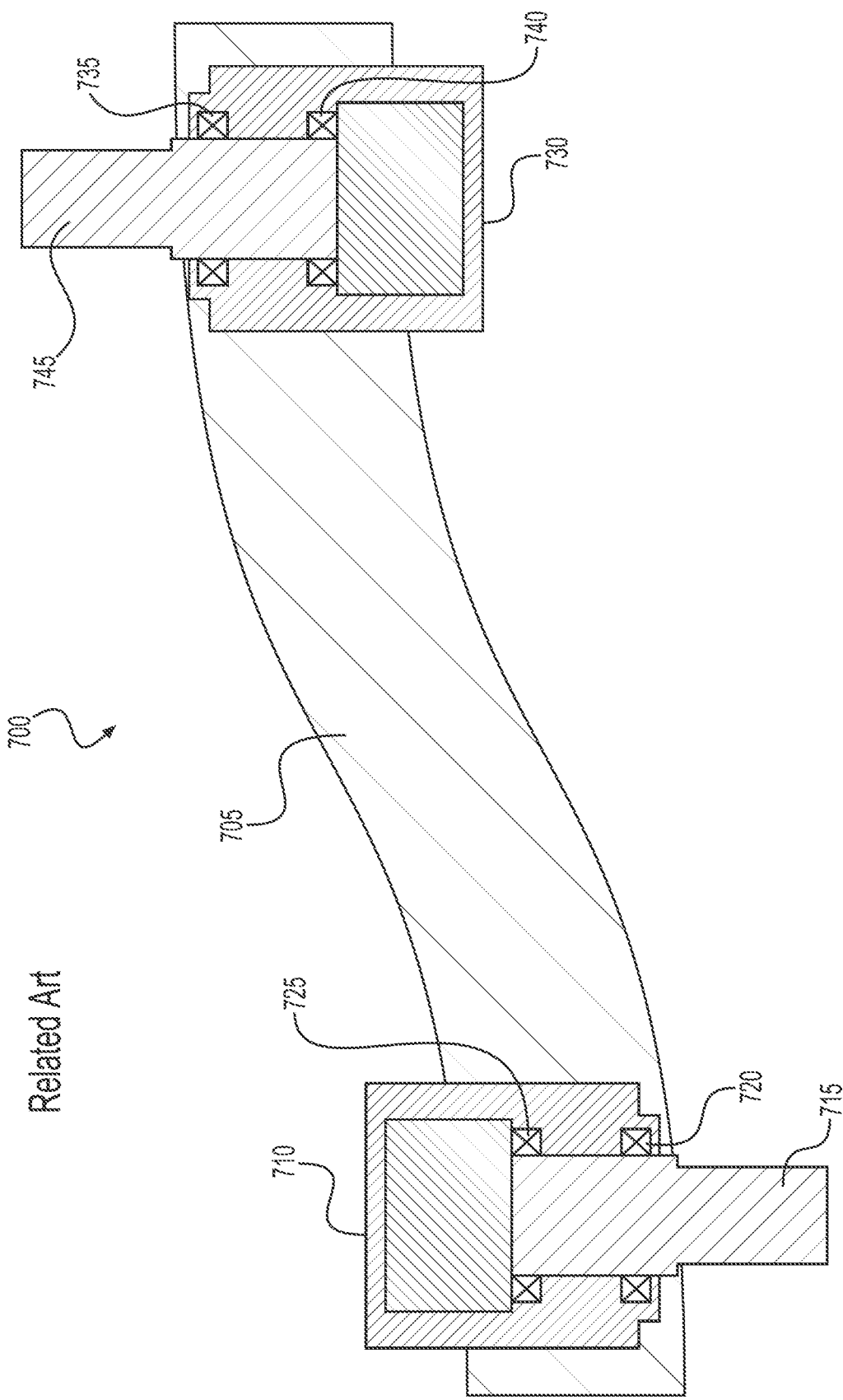
FIG. 7 shows a carrier arm known from the related art.

FIG. 7 shows a carrier arm 700 known from the related art. Carrier arm 700 corresponds to carrier arm 220 in FIG. 2. As shown in FIG. 7, carrier arm 700 includes carrier arm body 705, shaft 715 which can be mounted pivotably in the bearing 215 of stand 201, for example, and shaft 745 on which bearing 225 of carrier arm 230 shown in FIG. 2 can be mounted.

Shafts 715 and 745 are pivotably mounted in bearings 720, 725, 735, and 740 which are provided inside assemblies 710 and 730. These assemblies also include locking mechanisms and are mounted in recesses on end faces of the carrier arm 705. As a result, a flow of force is only enabled through the end faces at which the assemblies 710 and 730 are mounted respectively. As a consequence, bearings and carrier arm need to have a massive design to achieve the required stiffness.

By directly integrating the bearings into the structure of the carrier arm, the contour in the area of the bearings can be significantly reduced. This also reduces the radial installation space of the covers and thus improves the overall disturbance contour.

Figure 8:
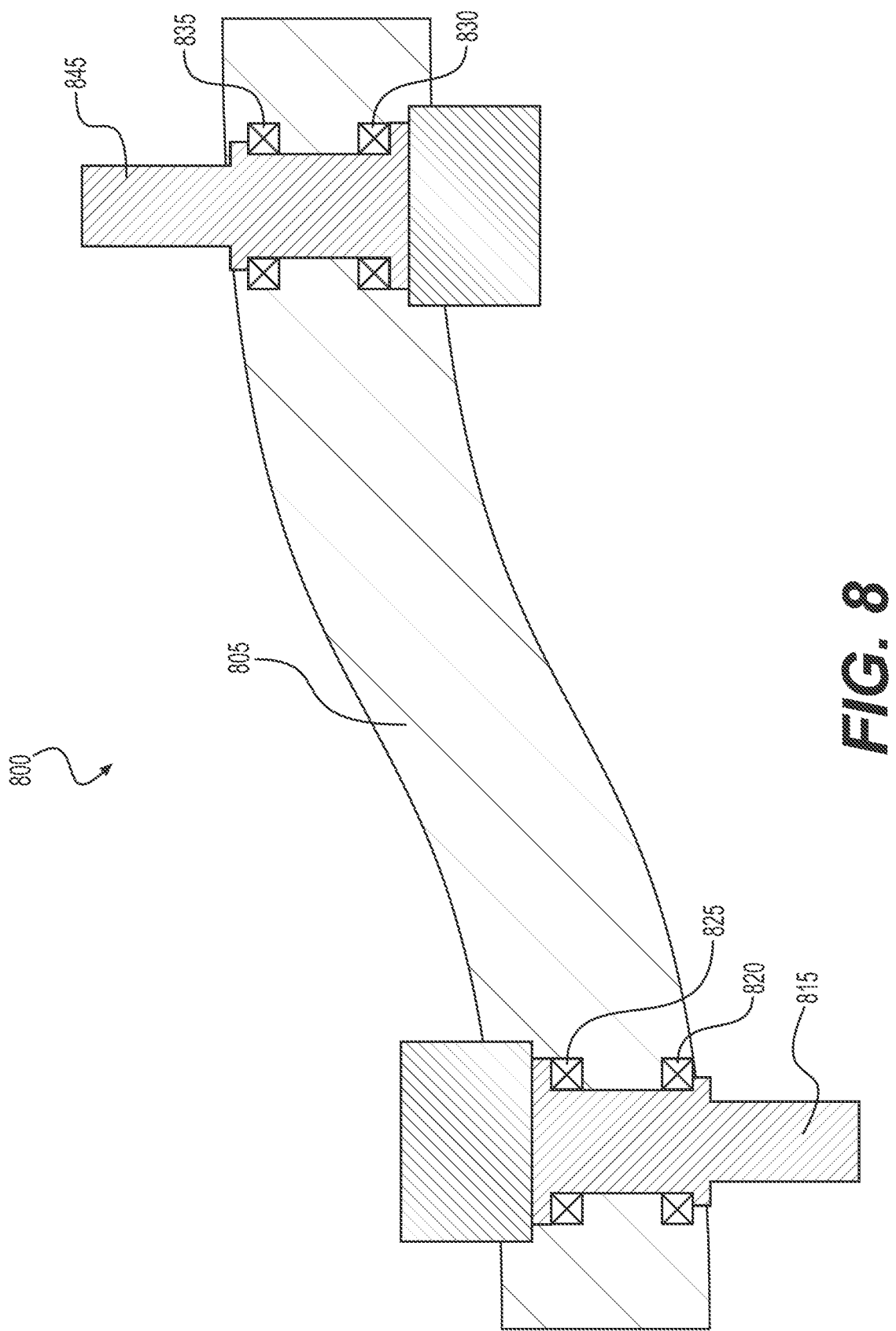
FIG. 8 shows a carrier arm according to an exemplary embodiment of the disclosure.

FIG. 8 shows a carrier arm 800 with carrier arm body 805 according to an exemplary embodiment of the disclosure in which bearings 820, 825, 830, and 835 are directly integrated in the carrier arm body 805. Shafts 815 and 845 are pivotably mounted in bearings 820, 825, 830, and 835. Notably, this exemplary embodiment dispenses with the assemblies 710 and 730 shown in FIG. 7 which allows a direct flow of force from the bearings to the body of the carrier arm 805. As a result, the radial installation space of the covers is reduced and thus the overall disturbance contour is improved.

Reference is now made to FIG. 9 (with continued reference to FIGS. 2 and 3) which shows a flow chart of a method 900 for optimizing an assembly space of a surgical microscopy system. The method begins at 905 at which a plurality of electronic components 260 and 285 is relocated from a plurality of arms 220 and 230 to an area between a bearing 315 and a base part 395 of a stand part 305 thereby shifting a center of gravity of a stand from a first center position 210 to a second center position 310.

The method continues to step 910 at which the plurality of electronic components 360 and 385 is connected to the at least one mounting element 515 (shown in FIG. 5) on the stand part 500 (which corresponds to stand part 305).

It is understood that the foregoing description is that of the exemplary embodiments of the invention and that various changes and modifications may be made thereto without departing from the spirit and scope of the invention as defined in the appended claims.

What is claimed is:

1. A stand for a surgical microscope comprising:
a base part;
a stand part forming a c-shape structure in a cross section taken in a plane perpendicular to a height direction of the stand, having a first end and a second end, and being mounted on the base part at the first end;
the stand part having a hollow structure with reinforcements arranged within the hollow structure and the reinforcements vertically extending through the entire hollow structure,
wherein the stand part includes a first stand part element and a second stand part element, and
wherein the first and second stand part elements are arranged at a horizontal distance relative to one another and form together the c-shape structure.

2. The stand of claim 1, wherein the stand part includes a connecting part arranged at the second end of the of the stand part,
a plurality of mounting elements arranged on inner surfaces of the first and second stand part elements to mount at least one electronic component on the stand part between the connecting part and the base part, and
a cover which encloses the at least one electronic component.

3. The stand of claim 2, wherein the at least one electronic component includes a personal computer, a video device, a power supply device, a light source, a network interface component, and a radio-frequency identification (RFID) reader.

4. The stand of claim 2, further comprising:
a plurality of arms arranged on the stand part;
the plurality of arms being connected to one another by rotary joints defining at least three rotation axes and being configured to displace a surgical microscope head, mounted on one of the plurality of arms via a suspension mechanism, in three directions of a coordinate system.

5. The stand of claim 4, wherein:
the plurality of arms includes a carrier arm,
the carrier arm includes at least one first bearing and at least one second bearing, a first shaft arranged in the at least one first bearing, and a second shaft arranged in the at least one second bearing, and
the at least one first bearing and the at least one second bearing are directly mounted on the carrier arm.

6. The stand of claim 5, wherein:
the carrier arm is a first carrier arm,
the plurality of arms includes a second carrier arm having a third bearing,
the first shaft is arranged in a recess on the connecting part and defines a first rotation axis of the at least three rotation axes, and
the second shaft is arranged in the third bearing and defines a second rotation axis of the at least three rotation axes.

7. A surgical microscopy system comprising:
a stand including a base part and a stand part;
the stand part including a first stand part element and a second stand part element and having a first end and a second end;
the stand part being mounted on the base part at the first end;
the stand part including a plurality of mounting elements arranged on inner surfaces of the first and second stand part elements;
the first and second stand part elements being arranged at a horizontal distance relative to one another and forming together a c-shape structure in a cross section taken in a plane perpendicular to a height direction of the first and second stand part elements;
each of the first and second stand part elements having a hollow structure with reinforcements arranged within the hollow structure and the reinforcements vertically extending through the entire hollow structure;
a bearing arranged at the second end of the stand part;
at least one electronic component arranged between the bearing and the base part and being connected to the at least one mounting element on the stand part;
a plurality of arms arranged on the stand part;
a surgical microscope head mounted on one of the plurality of arms;
the plurality of arms being connected to one another by rotary joints defining at least three rotation axes and being configured to displace the surgical microscope head in three directions of a coordinate system.

8. The surgical microscopy system of claim 7, wherein the at least one electronic component includes a personal computer, a video device, a power supply device, a light source, a network interface component, and a radio-frequency identification (RFID) reader.

9. The surgical microscopy system of claim 6, wherein:
the plurality of arms includes a carrier arm,
the carrier arm includes at least one first bearing and at least one second bearing, a first shaft arranged in the at least one first bearing, and a second shaft arranged in the at least one second bearing, and
the at least one first bearing and the at least one second bearing are directly mounted on the carrier arm.

10. The surgical microscopy system of claim 9, wherein:
the carrier arm is a first carrier arm,
the plurality of arms includes a second carrier arm having a third bearing, the first shaft is arranged in a recess on the connecting part and defines a first rotation axis of the at least three rotation axes, and the second shaft is arranged in the third bearing and defines a second rotation axis of the at least three rotation axes.

11. A method for optimizing an assembly space of a surgical microscopy system, the surgical microscopy system including a stand including a base part and a stand part, the stand part including a first stand part element and a second stand part element and having a first end and a second end, the stand part being mounted on the base part at the first end, the stand part including a plurality of mounting elements arranged on inner surfaces of the first and second stand part elements, the first and second stand part elements being arranged at a horizontal distance relative to one another and forming together a c-shape structure in a cross section taken in a plane perpendicular to a height direction of the first and second stand part elements, each of the first and second stand part elements having a hollow structure with reinforcements arranged within the hollow structure and the reinforcements vertically extending through the entire hollow structure, a connecting part arranged at the second end of the stand part, a plurality of arms arranged on the stand part, a surgical microscope head mounted on one of the plurality of arms, the plurality of arms being connected to one another by rotary joints defining at least three rotation axes and being configured to displace the surgical microscope head in three directions of a coordinate system, and a plurality of electronic components arranged on the plurality of arms, the method comprising:

relocating the plurality of electronic components from the plurality of arms to an area between the connecting part and the base part of the stand part thereby shifting a center of gravity of the stand from a first center position to a second center position;

and connecting the plurality of electronic components to the at least one mounting element on the stand part.

12. The method of claim 11, wherein:

the first center position is defined at a first horizontal distance and a first vertical distance from a center of the base part based on first locations of the plurality of electronic components on the plurality of arms, the second center position is defined at a second horizontal distance and a second vertical distance from the center of the base part based on second locations of the plurality of electronic components in the area between the connecting part and the base part of the stand part, the first horizontal distance is larger than the second horizontal distance, and the first vertical distance is larger than the second vertical distance.

13. The method of claim 11, further comprising:

reducing motion forces required for positioning the surgical microscopy head in the surgical microscopy system by the shifting of the center of gravity of the stand from the first center position to the second center position and by the connecting of the plurality of electronic components to the at least one mounting element on the stand part.

14. The method of claim 11, further comprising:

reducing a drift of the surgical microscopy head by the shifting of the center of gravity of the stand from the first center position to the second center position and by the connecting of the plurality of electronic components to the at least one mounting element on the stand part.

15. The method of claim 11, wherein the plurality of electronic components includes a personal computer, a video device, a power supply device, a light source, a network interface component, and a radio-frequency identification (RFID) reader.

16. The method of claim 11, wherein:

the plurality of arms includes a carrier arm, the carrier arm includes at least one first bearing and at least one second bearing, a first shaft arranged in the at least one first bearing, and a second shaft arranged in the at least one second bearing, and the method further comprises:

directly mounting the at least one first bearing and the at least one second bearing on the carrier arm, and reducing an interfering contour of the carrier arm by reducing a cross section of the carrier arm, the interfering contour being a contour which interferes with a field of view of a person operating the surgical microscopy system.

17. The method of claim 16, further comprising:

reducing the interfering contour of the surgical microscopy system by:

the relocating of the plurality electronic components from the plurality of arms to the area between the connecting part and the base part of the stand part, and the reducing of the cross section of the carrier arm.

* * * * *